United States Patent [19]

Müller et al.

[11] 4,156,636

[45] May 29, 1979

[54] PROCESS FOR THE PRODUCTION OF LOW MOLECULAR WEIGHT POLYHYDROXYL COMPOUNDS

[75] Inventors: Hanns P. Müller; Kuno Wagner, both of Leverkusen, Fed. Rep. of Germany

[73] Assignee: Bayer Aktiengesellschaft, Leverkusen, Fed. Rep. of Germany

[21] Appl. No.: 934,567

[22] Filed: Aug. 17, 1978

[30] Foreign Application Priority Data

Aug. 26, 1977 [DE] Fed. Rep. of Germany ....... 2738512

[51] Int. Cl.$^2$ ........................ C25B 3/04; C07C 47/19; C07C 49/17; C07C 29/14
[52] U.S. Cl. .................................... 204/77; 260/594; 260/602; 568/863
[58] Field of Search ................ 568/863; 260/594, 602; 204/77

[56] References Cited

U.S. PATENT DOCUMENTS

| | | | |
|---|---|---|---|
| 2,224,910 | 12/1940 | Hanford et al. | 260/594 |
| 2,269,935 | 1/1942 | Hanford et al. | 260/594 |
| 2,760,983 | 8/1958 | MacLean et al. | 260/594 |

*Primary Examiner*—Joseph E. Evans
*Attorney, Agent, or Firm*—Gene Harsh; Joseph C. Gil

[57] ABSTRACT

Low molecular weight polyhydroxyl compounds are made from formaldehyde hydrate by an improved process comprising adjusting the pH of an aqueous solution of formaldehyde and co-catalyst to 9–12 with calcium hydroxide at 80°–110° C. to begin condensation and then adding to this reaction mixture aqueous formalin and/or paraformaldehyde and calcium hydroxide to maintain a pH of 7.5–9.5 and temperature of 80°–110° C.

11 Claims, No Drawings

PROCESS FOR THE PRODUCTION OF LOW MOLECULAR WEIGHT POLYHYDROXYL COMPOUNDS

BACKGROUND OF THE INVENTION

Polyhydroxyl compounds have acquired considerable commercial significance in a variety of different fields. They are commercially used, for example, for the production of non-ionic surface-active compounds, as anti-freeze agents, humectants, plasticizers and as starting components for plastics, such as polyester and polyether resins.

Polyhydric alcohols are currently obtained from naturally occurring substances, such as sugar or cellulose materials, or are synthesized by the oxidation of petroleum derivatives.

In view of the world food situation, however, it would appear to be poor policy to use naturally occurring materials (which may be used as a carbohydrate source in foods) as starting materials for commercial products. On the other hand, due to the shortage of petroleum resources, the prices of products dependent upon petroleum have steadily increased. In addition, there is no guarantee of the longterm availability of petroleum products. Accordingly, it is desirable to find production processes for polyhydroxyl compounds of which the raw material supply is dependent neither upon naturally occurring materials nor upon petroleum.

Since the works of Butlerow and Loew (ann. 120, 295 (1861) and J. pr. Chem. 33, 321 (1886)) it has been known that hydroxy aldehydes and hydroxy ketones are formed by the auto-condensation of formaldehyde hydrate (hereinafter the expression "auto-condensation of formaldehyde" is always intended to mean the "auto-condensation of formaldehyde hydrate") under the influence of basic compounds, such as calcium or lead hydroxide. Since formaldehyde may be obtained from coal or natural gas by way of methanol, this would, in principle, be one method of obtaining hydroxyl group-containing compounds from which polyhydric alcohols may be synthesized independent of petroleum. The method would be by electrolytic reduction or by catalytic and chemical hydrogenation.

However, despite numerous proposals for the synthesis of polyhydroxyl compounds by the auto-condensation of formaldehyde, no commercially workable process has as yet been developed for this purpose because it has not yet been possible to synthesize mixtures of polyhydroxyl compounds with defined reproducibility of the hydroxyl functionality. In addition, the hydroxy aldehyde and hydroxy ketone mixtures obtained in conventional processes require the use of large quantities of catalyst and are difficult to hydrogenate. This high consumption of catalyst has hitherto made the synthesis of polyhydroxyl compounds by the auto-condensation of formaldehyde hydrate appear uneconomic and has prevented the auto-condensation of formaldehyde hydrate from being used as the basis of a commercial process for the synthesis of polyhydric alcohols.

Due to the simultaneous disproportionation of the formaldehyde into methanol and formic acid, it has only been possible to obtain moderate yields by the conventional processes. Considerable costs are involved in working-up the aqueous or aqueous/alcoholic solutions formed.

The disproportionation of formaldehyde into methanol and formic acid is known to be catalyzed to a very considerable extent by basic compounds. As Pfeil, Chemische Berichte 84. 229 (1951) found, the reaction velocity of this so-called "Cannizzaro reaction" is dependent upon the square of the formaldehyde concentration, while the velocity of the formaldehyde polyaddition reaction (C-C-linkage) is a linear function of the formaldehyde concentration (Pfeil and Schroth, Chemische Berichte 85, 303 (1952)). Accordingly, with increasing aldehyde concentration, the desired quantitative ratio of polyhydroxyl compounds to methanol and formic acid is not obtained. Accordingly, in most conventional processes, condensation of the formaldehyde into hydroxy aldehydes and hydroxy ketones is carried out in solutions having low formaldehyde concentrations. However, in order to recover the hydroxy aldehydes and hydroxy ketones formed, the water used as solvent must be removed by distillation. This gives rise to considerable energy costs due to the considerable heat of evaporation of the water. For this reason, processes for condensing formaldehyde from dilute aqueous solutions are uneconomical. In addition, decomposition and discoloration reactions involving the hydroxy aldehydes and hydroxy ketones formed generally occur during the prolonged distillation times.

It is therefore desirable to carry out the condensation of formaldehyde from standard commercial-grade concentrated formalin solutions without troublesome secondary reactions. German Pat. No. 822,385 describes a process for the production of aliphatic oxyaldehydes, in which a 40% formalin solution is reacted with thallium or thallium hydroxide. However, this process is objectionable in view of the toxicity and availability of thallium. Moreover, the yields of this process, of from 70 to 80%, are relatively low.

In order to avoid the Cannizzaro reaction, it has also been proposed to react formaldehyde solutions with calcium or lead hydroxide in the presence of methanol, ethanol or other polar organic solvents (German Pat. No. 830,951 and Gorr and Wagner, Biochemische Zeitschrift, 262 261 (1933)). However, by adding organic solvents, the formaldehyde content of the solution is again reduced. The additional energy costs involved in evaporating the solvent added during working-up of the hydroxy aldehydes and ketones formed also make these processes uneconomical. In addition, substantially unstable semi-acetals are formed from formaldehyde and lower alcohols, decomposing during the condensation reaction.

German Pat. No. 884,794 describes a process for the production of oxy-oxo compounds, in which up to 30% aqueous formaldehyde solutions are reacted with lead oxide or lead acetate and inorganic bases to form sugar-like compounds which reduced Fehling's solution at cold temperatures. In this process, however, the formaldehyde solution has to be heated for from 7 to 8 hours. For this reason, the volume-time yield obtained is unsatisfactory. The relatively poor yields (about 80%, based on the formaldehyde used) are also unsatisfactory.

U.S. Pat. No. 2,224,910 describes a process for the production of hydroxy aldehydes and hydroxy ketones, in which the exothermic auto-condensation of the formaldehyde is controlled by the measured addition of inorganic or organic bases to a formaldehyde solution containing lead, tin, calcium, barium, magnesium, cerium or thorium compounds and a compound capable of enediol formation, such as glucose, ascorbic acid, fructose, benzoin, glycol aldehyde, erythrose, reductose, invert sugar or condensation products of formaldehyde. Although a mixture of hydroxy aldehydes and hydroxy ketones is obtained from formaldehyde solutions of relatively high concentration without the addition of organic solvents in this process, various disadvantages exist. When the reaction is carried out at low pH values, substantial quantities of hydroxy aldehyde and hydroxy ketone mixtures of low hydroxy functionality are obtained. In addition, only moderate reaction velocities are obtained at low pH values, so that the volume-time yields of the process are generally unsatisfactory. In order to obviate these disadvantages, it is recommended in the above-mentioned patent to start condensation of the formaldehyde at low pH values and then to complete the condensation at higher pH values. At pH values of $\geq 7$, however, the lead-catalyzed autocondensation of the formaldehyde takes place spontaneously and uncontrollably. It is, thus, not possible by this process to obtain mixtures of hydroxy aldehydes and hydroxy ketones with a reproducible component distribution. In addition, it is known that hydroxy aldehydes, hydroxy ketones and mono-saccharides decompose in alkaline medium and at elevated temperature to form dark colored compounds partially containing carboxyl groups.

These decomposition reactions occur in the processes suggested as preferred in U.S. Pat. No. 2,224,910, especially after most of the formaldehyde has reacted. Accordingly, hydroxy aldehyde and hydroxy ketone mixtures so produced contain decomposition products having acid groups, are brown in color and cannot be reproducibly obtained. In addition, these mixtures may only be hydrogenated using uneconomically large quantities of Raney nickel catalyst. For example, 30 g of Raney nickel are required for hydrogenating a quantity of hydroxy aldehyde and hydroxy ketone mixture equivalent to 100 g of formaldehyde.

For purification and for recovering hydroxyl compounds of low molecular weight, the product mixture obtained by the process just described always must be worked-up by distillation. This distillation necessarily involves additional energy and plant costs. It would be desirable to produce the product mixtures in such a way that they might be directly used after removal of the solvent water without any need for distillation. However colorless reaction mixtures substantially free from secondary products cannot be obtained by conventional processes.

Accordingly, an object of the present invention is to provide a process by which it is possible to synthesize mixtures of polyhydroxyl compounds which are substantially free from decomposition products and which may readily by hydrogenated using small quantities of hydrogenation catalysts to form polyhydric alcohols. The mixtures of polyhydroxyl compounds obtained should be colorless and should not require further purification.

Another object of the present invention is to control the auto-condensation of formaldehyde in such a way that the product distribution of the mixtures of low molecular weight polyhydroxyl compounds formed may be varied and reproducibly adjusted as required.

The term "formose" in the context of the present invention means the known mixtures of low molecular weight polyhydroxyl compounds (polyhydric alcohols, hydroxy aldehydes and hydroxy ketones) which are produced by the auto-condensation of formaldehyde hydrate.

DESCRIPTION OF THE INVENTION

It has now surprisingly been found that colorless formoses substantially free from troublesome secondary products may be obtained in high volume/time yields by carrying out the condensation of formaldehyde hydrate at basic pH values in the presence of (a) calcium hydroxide as catalyst and (b) compounds capable of enediol formation as cocatalyst. The concentration of formaldehyde in the reaction mixture must be controlled by metering the aqueous formalin solution and/or paraformaldehyde dispersion used as formaldehyde source at a suitable rate in such a way that the formaldehyde concentration does not fall below or exceed a certain minimum or maximum value, based on the reaction mixture as a whole. It may be regarded as particularly surprising that, despite the high pH values, there are no browning or decomposition reactions involving the formose and that Cannizzaro reactions are suppressed to a considerable extent. The formoses formed have a relatively high content of reducing groups.

Accordingly, the present invention relates to a process for the production of low molecular weight polyhydroxyl compounds by condensing formaldehyde hydrate in the presence of calcium hydroxide as catalyst and compounds capable of enediol formation as cocatalyst. A formaldehyde containing solution of the cocatalyst in water and, optionally, low molecular weight monohydric or polyhydric alcohols and/or relatively high molecular weight polyhydroxyl compounds is adjusted to a pH value of from 9 to 12, preferably from 9 to 10, by the addition of calcium hydroxide at a temperature of from 80° to 110° C., preferably from 90° to 105° C., so that condensation of the formaldehyde hydrate is initiated. An aqueous formalin solution and/or paraformaldehyde dispersion containing from 20 to 65%, by weight, of formaldehyde and calcium hydroxide are then introduced in such a quantity that the reaction mixture is maintained at a pH value of from 7.5 to 9.5, preferably from 8 to 9, at a temperature of from 80° to 110° C., preferably from 90° to 105° C. The concentration of formaldehyde is maintained at from 0.5 to 10%, by weight, preferably from 1.2 to 6%, by weight, based on the reaction mixture as a whole, throughout the condensation reaction. Finally, the residual quantity of formaldehyde, amounting to from 0.05 to 10%, by weight, is optionally removed by further condensation at pH values below 7 or by reaction with other compounds that are reactive with formaldehyde hydrate.

As mentioned above, it is essential to the present invention that the formaldehyde be present in relatively low concentrations, based on cocatalyst or on the reaction mixture as a whole, from the very beginning of the condensation reaction. On the other hand, however, the concentration of formaldehyde should never fall below the minimum concentration specified above because otherwise browning reactions occur with formation of troublesome secondary products.

The pH profile claimed is not critical. Whereas the reaction is preferably started at pH values of from 9 to 10 (pH ranges above 12 should be avoided because the small quantity of formaldehyde used at the beginning of the reaction should be consumed too quickly with the result that the condensation reaction becomes difficult to control), the condensation reaction is subsequently continued by metering the calcium hydroxide at a suitable rate to maintain a pH value of from 7.5 to 9.5, preferably from 8 to 9. The reaction mixture is preferably permanently maintained at boiling temperature. At pH values above 9.5, the reaction is difficult to control. At pH values below 7.5, not only is the reaction time considerably increased but the consumption of calcium hydroxide is also surprisingly higher.

After the required quantity of aqueous formalin solution or paraformaldehyde dispersion has been added, the condensation reaction is terminated in known manner by cooling or by the addition of an acid (preferably sulphuric acid or oxalic acid, because in this way the calcium ions are simultaneously precipitated). However, the condensation reaction may also be continued at pH values below 7 until the formaldehyde has been completely consumed. It is also possible to remove the formaldehyde residue present at the end of the reaction according to the present invention, amounting to at least 0.5%, by weight, of formaldehyde, based on the reaction mixture, by reaction with methylolatable compounds, such as aminoplast monomers, phenoplast monomers, dialkyl phosphites or aldolatable carbonyl compounds, as explained in more detail below. For numerous applications, this crude formose then must be desalted by passage over anion and cation exchangers and concentrated to the required water content.

It is surprising that highly concentrated aqueous solutions of polyols, hydroxy aldehydes and hydroxy ketones which are completely colorless and, therefore, require no further purification or decoloration are obtained in yields of up to 95% and with high reproducibility of the average OH-functionality. In contrast strongly colored, troublesome secondary products are formed as a result of decomposition reactions in conventional processes. These secondary products may only be removed, if at all, with considerable effort and high additional outlay. In addition, these strongly colored solutions of the prior art may only be hydrogenated, if at all, to form polyhydric alcohols with considerable effort and in low yields. In contrast, the colorless reaction mixtures according to the present invention may be catalytically hydrogenated under mild conditions, such as are generally applied in the catalytic hydrogenation of sugars, following removal of the catalyst by simple precipitation reactions.

In the process according to the present invention, glycol aldehyde is initially formed in a first step from 2 molecules of formaldehyde. By further addition of formaldehyde, glycerol aldehyde is formed therefrom in accordance with the following scheme:

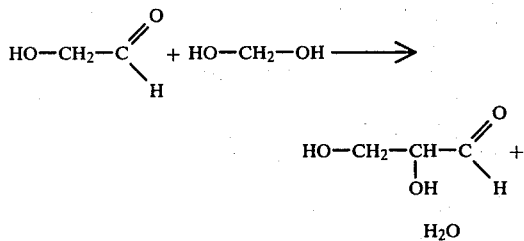

In a number of secondary reactions, of which only a few are exemplified, the mixtures of hydroxy aldehydes and ketones obtainable in accordance with the present invention are formed from the thus-obtained glycerol aldehyde:

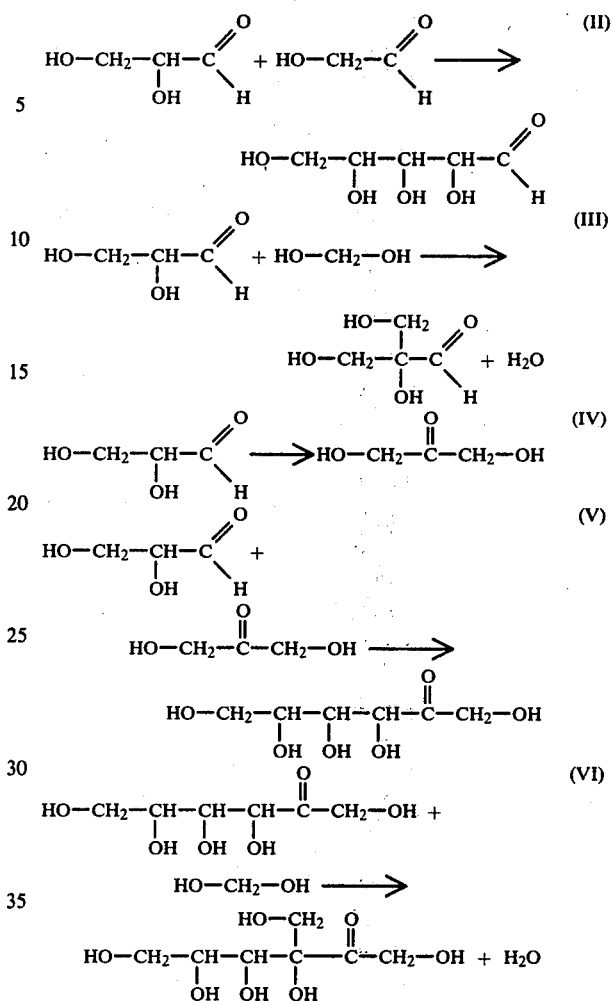

As shown by gas chromatographic analysis of various product mixtures obtained in accordance with the present invention, it is possible to vary the product distribution by terminating the reaction at different residual formaldehyde contents. It is also possible to adjust the product distribution in a totally reproducible manner both in the case of compounds containing from 2 to 4 carbon atoms and also in the case of compounds containing 5 and more carbon atoms. This had not been expected from the large number of reactions which take place simultaneously during the process according to the present invention.

The formaldehyde is preferably condensed from aqueous formaldehyde solutions of standard commercial concentration (from 30 to 50%, by weight, of formaldehyde) which are stabilized by methanol or other known stabilizers. However, it is also possible to use non-stabilized formaldehyde solutions containing fractions of solid, polymerized formaldehyde and/or paraformaldehyde dispersions. These solids are dissolved by depolymerization during the process according to the present invention and are also condensed to form hydroxy aldehydes and hydroxy ketones. Condensation may also be carried out from even more highly concentrated formaldehyde solutions which may be produced, for example, by the depolymerization of paraformaldehyde or by concentrating formaldehyde solutions of low concentration in vacuo. For example, hydroxy aldehydes and hydroxy ketones may be obtained in very high yields by condensing a 65% formaldehyde solution obtained by concentrating a 37% formaldehyde solution in vacuo. The process according to the present invention may, of course, also be applied to less concentrated formaldehyde solutions. The use of these low concentration formaldehyde solutions, however, is less preferred from an economical point of view because of the additional energy costs involved in evaporating the solvent.

The condensation reaction of the formaldehyde hydrate is started by means of aqueous cocatalyst solutions which contain from 0.5 to 10%, by weight, preferably from 1.2 to 6%, by weight, of formaldehyde. The concentration of the cocatalyst in this starter mixture generally amounts to from 2 to 90%, by weight, preferably from 10 to 80%, by weight, and, with particular preference, from 20 to 60%, by weight. According to the present invention, suitable cocatalysts are any known compounds containing enediol groups and compounds capable of forming enediols in accordance with the equation:

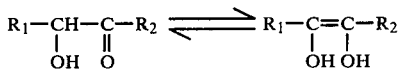

wherein $R_1$ and $R_2$ represent hydrogen, alkyl, hydroxyalkyl or aryl groups.

Examples of such compounds include glucose, fructose, ascorbic acid, benzoin, glycol aldehyde, glycerol aldehyde, erythrose, invert sugar and the like. However, cocatalysts preferably used in accordance with the present invention are formoses, particularly those which are characterized by the following molar ratios:

Compounds containing 3 carbon atoms/compounds containing 4 carbon atoms: 0.5:1–2.0:1
Compounds containing 4 carbon atoms/compounds containing 5 carbon atoms: 0.2:1–2.0:1
Compounds containing 5 carbon atoms/compounds containing 6 carbon atoms: 0.9:1–5.0:1 the proportion of components containing from 3 to 6 carbon atoms amounting to at least 75%, by weight, preferably more than 85%, by weight, based on the total cocatalyst.

Since all these cocatalysts contain numerous free hydroxyl groups, the formaldehyde present at the start of the reaction is largely in the form of semi-acetals with these hydroxyl compounds.

In addition to compounds capable of enediol formation and formaldehyde, the starter mixture may also contain monohydric or polyhydric alcohols having molecular weights of up to about 400 and even relatively high molecular weight polyhydroxyl compound. In this connection, suitable low molecular weight alcohols include methanol, ethanol, isopropanol, n-butanol, t-butanol, neopentyl alcohol, ethylene glycol monomethyl ether, ethylene glycol monoethyl ether, ethylene glycol, 1,2- and 1,3-propylene glycol, 1,4- and 2,3-butylene glycol, 1,6- and 2,3-hexane diol, 2-methyl-1,2-propane diol, 1,2,4-butane triol, 1,2,6-hexane triol, glycerol, erythritol, quinitol, mannitol, sorbitol and methyl glycoside, addition products of ethylene oxide and/or propylene oxide with these alcohols, and the like. It is preferred to use polyhydric alcohols containing at least two adjacent hydroxyl groups. Suitable relatively high molecular weight polyhydroxyl compounds include those described below as starting components for the production of polyurethane plastics. These polyhydroxyl compounds may, of course, also be added to the reaction mixture during the process according to the present invention, i.e. at the same time as the formaldehyde and the calcium hydroxide.

The reaction according to the present invention may even be started in the absence of compounds capable of enediol formation providing the starter mixture contains polyols containing at least two vicinal hydroxyl groups. This procedure is similar to that described in German Offenlegungsschrift No. 2,714,104.

Products of different functionality and average molecular weight are obtained, depending upon the concentration of formaldehyde maintained in the reaction mixture during the process according to the present invention. Thus, when the formaldehyde concentration is maintained relatively low and the condensation reaction is continued to a residual formaldehyde content of, or only slightly more than, 0.5% by weight, products containing 5, 6 or 7 carbon atoms are primarily obtained. In addition, methylolation reactions occur on the carbon atoms in the α-position to the carbonyl groups of the formose. This gives rise to the formation of branched sugars. If, however, relatively high formaldehyde concentrations (of the order of 10%, by weight, based on the total reaction mixture) are maintained during the process and if the reaction is stopped at high residual formaldehyde contents, the product mixture formed contains only a few compounds having 6 or more carbon atoms. By contrast, the proportion of compounds containing from 2 to 4 carbon atoms is considerably increased. In this way, it is possible to obtain a variety of different product distributions by carrying out auto-condensation of the formaldehyde with different concentrations of formaldehyde and continuing the reaction to different residual formaldehyde contents. It is possible in this way to establish any desired product distribution which is required for any specified application.

Mixtures containing major amounts of relatively high molecular weight products are also obtained by subsequently after-treating hydroxy aldehyde and hydroxy ketone mixtures containing major amounts of low molecular weight fractions with excess formaldehyde for from about 10 minutes to 12 hours, in the presence of an inorganic or organic base, at a pH value of from 9 to 13, preferably from 10 to 11, and at temperatures of from 10° to 100° C., preferably from 30° to 60° C. In this way, not only are the low molecular weight compounds converted into compounds of relatively high molecular weight by an alkali-catalyzed aldol reaction, but branched hydroxy aldehydes and hydroxy ketones are also formed to an increased extent by additional methylolation on the carbon atom adjacent the carbonyl group. These branched hydroxy ketones and hydroxy aldehydes contain considerably more primary hydroxyl groups than the linear products. The reactivity of these mixtures compared to typical reactants containing hydroxyl groups is thus considerably increased, which is advantageous for some applications. For example, when the compounds produced in accordance with the present invention are reacted with organic isocyanates, urethanes are formed much more quickly due to the presence of primary OH-groups than is the case with normal, straight-chain polyhydric alcohols containing secondary OH-groups.

Tertiary amines, such as triethylamine, tripropylamine or dimethyl benzyl amine, are particularly suitable for this subsequent α-methylolation of the formoses obtained in accordance with the present invention.

Polyhydric alcohols may readily be obtained by reduction in known manner from the hydroxy aldehydes and hydroxy ketones formed in the process according to the present invention. For example, reduction may be carried out directly with sodium borohydride from the aqueous solution obtained, even at temperatures as low as room temperature. However, it may also be carried out, for example, electrolytically. Catalytic hydrogenation using hydrogen is also possible. In principle, any of the conventional processes used for the reduction of sugars into sugar alcohols may be used for this purpose. Hydrogenation using Raney nickel in quantities of from 5 to 20%, by weight, based on the hydroxy aldehyde and hydroxy ketone mixture to be reduced, under hydrogen pressures of from 50 to 200 kg/cm$^2$ and at temperatures of from 20° to 200° C. is particularly suitable. Catalysts containing nickel, cobalt, copper, platinum, rhodium or palladium on inert supports may also be used. These reduced formoses are referred to hereinafter as "formitols".

It is also possible to reduce the hydroxy aldehydes and ketones present in the formoses obtained in accordance with the present invention with formaldehyde. To this end, excess formaldehyde and an inorganic base are added to the reaction solution which is then stirred for from 30 minutes to 12 hours at from 10° to 100° C., preferably from 30° to 60° C., and at a pH value maintained at from 9 to 13, preferably from 10 to 11. In this case, it is possible not only to reduce the carbonyl function, but at the same time to synthesize relatively high molecular weight and branched products. Preferred inorganic bases which accelerate the Cannizzaro reaction are sodium hydroxide, potassium hydroxide, calcium and barium hydroxide, "crown ether" complexes of alkali atoms and the like.

The reduction reaction may be further accelerated by cocatalysts. Cocatalysts preferably used for this purpose are oxalates of transition metals, particularly nickel, cobalt, iron, cadmium, zinc, chromium and manganese oxalate, as well as transition metals in elemental form such as nickel, cobalt, iron, copper, cadmium, zinc, chromium and manganese. Activated nickel, which is used in the form of so-called "Raney nickel", and elemental zinc in powder form are especially preferred.

Other suitable cocatalysts for the reduction reaction with formaldehyde are amides of organic acids, such as formamide, dimethyl formamide and acetamide, as well as tetraalkyl ammonium salts, particularly tetramethyl ammonium chloride and tetraethyl ammonium chloride.

As mentioned above, the residual formaldehyde still present in the formose at the end of the process may be removed not only by further condensation in a neutral or weakly basic pH range, but also by the addition of methylolatable compounds. Such compounds include aldehydes and ketones containing a hydrogen atom in the α-position to the carbonyl group, such as acetaldehyde, butyraldehyde, isobutyraldehyde, methylethyl ketone, acetone, cyclopentanone, cyclohexanone, mesityl oxide, isophorone, acetophenone, acetoacetic ester and the like. In this connection, it is preferred to use butyraldehyde, isbutyraldehyde, acetone and cyclohexanone.

According to the present invention, however, the residual formaldehyde may also be taken up by compounds capable of forming aminoplasts which react with formaldehyde to form the corresponding N-methylol derivatives. Suitable aminoplast monomers are known and are described, for example, in German Offenlegungsschrift No. 2,324,134. In this connection, it is preferred to use urea, thiourea, ε-caprolactam, bisurethanes, oxamide, pyrrolidone, dicyanodiamide, melamine, phenols, naphthols, bisphenol-A, phenol and naphthol sulphonates.

The residual formaldehyde may also be removed by the addition of dialkyl phosphites, particularly dimethyl phosphite and diethyl phosphite, resulting in formation of the corresponding hydroxymethyl phosphonic acid esters.

The advantage of adding the above-mentioned methylolatable compounds is that they significantly reduce the viscosity of the formoses obtained in accordance with the present invention. In order to obtain this effect, it is also possible to add the above-mentioned methylolatable compounds (or even the methylolation products thereof) at the very start of the condensation reaction or at any time during the process.

The mixtures of hydroxy aldehydes and hydroxy ketones obtainable in accordance with the present invention and polyhydric alcohols obtained from them by the Cannizzaro reaction or by hydrogenation are valuable starting materials for a number of interesting practical products.

For example, the polyhydroxyl compounds obtained by reduction are eminently suitable for use as chain-extending agents and cross-linking agents in the production of polyurethane plastics from polyisocyanates, low molecular weight polyhydroxyl compounds and, optionally, relatively high molecular weight polyhydroxyl compounds, chain-extending agents, blowing agents, catalysts and other known additives.

In this connection, suitable polyisocyanates include the aliphatic, cycloaliphatic, araliphatic, aromatic and heterocyclic polyisocyanates described, for example, by W. Siefken in Justus Liebigs Annalen der Chemie, 562, pages 75 to 136. Examples include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate, and mixtures of these isomers; 1-isocyanato-3,3,5-trimethyl-5-isocyanatomethyl cyclohexane (German Auslegeschrift No. 1,202,785, U.S. Pat. No. 3,401,190); 2,4- and 2,6-hexahydrotolylene diisocyanate and mixtures of these isomers; hexahydro-1,3- and/or 1,4-phenylene diisocyanate; perhydro-2,4'- and/or 4,4'-diphenyl methane diisocyanate; 1,3- and 1,4-phenylene diisocyanate; 2,4- and 2,6-tolylene diisocyanate and mixtures of these isomers; diphenyl methane-2,4'- and/or -4,4'-diisocyanate; naphthylene-1,5-diisocyanate; triphenyl methane-4,4',4''-triisocyanate; polyphenyl polymethylene polyisocyanates, of the type which may be obtained by condensing aniline with formaldehyde, followed by phosgenation, and which are described, for example, in British Pat. Nos. 874,430 and 848,671; m and p-isocyanatophenyl sulphonyl isocyanates as described in U.S. Pat. No. 3,454,606; perchlorinated aryl polyisocyanates of the type described, for example, in U.S. Pat. No. 3,277,138; polyisocyanate containing carbodiimide groups of the type described in U.S. Pat. No. 3,152,162; diisocyanates of the type described in U.S. Pat. No. 3,492,330; polyisocyanates containing allophanate groups of the type described, for example, in British Pat. No. 994,890, Belgian Pat. No. 761,626 and published Dutch patent application No. 7,102,524; polyisocyanates containing isocyanurate groups of the type described, for example, in U.S. Pat. No. 3,001,973, German Pat. Nos. 1,022,789; 1,222,067 and 1,027,394 and in German Offenlegungsschriften Nos. 1,929,034 and 2,004,048; polyisocyanates containing urethane groups of the type described, for example, in Belgian Pat. No. 752,261 or in U.S. Pat. No. 3,394,164; polyisocyanates containing acylated urea groups as described in German Pat. No. 1,230,778; polyisocyanates containing biuret groups of the type described, for example, in U.S. Pat. Nos. 3,124,605 and 3,201,372 and in British Pat. No. 889,050; polyisocyanates obtained by telomerization reactions of the type described, for example, in U.S. Pat. No. 3,644,106; polyisocyanates containing ester groups of the type described, for example, in British Pat. Nos. 965,474 and 1,072,956, in U.S. Pat. No. 3,567,763 and in German Pat. No. 1,231,688; reaction products of the above-mentioned isocyanates with acetals as described in German Pat. No. 1,072,385; and polyisocyanates containing polymeric fatty acid radicals as described in U.S. Pat. No. 3,455,883.

It is also possible to use the isocyanate group-containing distillation residues obtained in the commercial production of isocyanates, optionally in solution in one or more of the aforementioned polyisocyanates. It is also possible to use mixtures of the aforementioned polyisocyanates.

In general, it is particularly preferred to use readily available polyisocyanates, such as 2,4- and 2,6-tolylene diisocyanate, and mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates").

Suitable relatively high molecular weight polyhydroxyl compounds, include those having molecular weights of from 800 to 10,000, preferably from 1000 to 6000, they include polyesters, polyethers, polythioethers, polyacetals, polycarbonates and polyester amides containing at least two, generally from 2 to 8, but preferably from 2 to 4, hydroxyl groups, of the type generally known and used for the production of homogeneous and cellular polyurethanes.

Examples of suitable polyesters containing hydroxyl groups are reaction products of polyhydric alcohols (preferably dihydric and, optionally, trihydric) with polybasic (preferably dibasic) carboxylic acids. Instead of the free polycarboxylic acids, the corresponding polycarboxylic acid anhydrides or corresponding polycarboxylic acid esters of lower alcohols or mixtures thereof may also be used for the production of the polyesters. The polycarboxylic acids may be aliphatic, cycloaliphatic, aromatic and/or heterocyclic, and may optionally be substituted, for example by halogen atoms, and/or they may be unsaturated. Examples of suitable polycarboxylic acids include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally in admixture with monomeric fatty acids, terephthalic acid dimethyl ester and terephthalic acid-bis-glycol ester. Examples of suitable polyhydric alcohols include: ethylene glycol, 1,2- and 1,3-propylene glycol, 1,4- and 2,3-butylene glycol, 1,6-hexane diol, 1,8-octane diol, neopentyl glycol, cyclohexane dimethanol (1,4-bis-hydroxymethyl cyclohexane), 2-methyl-1,3-propane diol, glycerol, trimethylol propane, 1,2,6-hexane triol, 1,2,4-butane triol, trimethylol ethane, pentaerythritol, quinitol, mannitol, sorbitol, methyl glycoside, also diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example ε-caprolactone, or hydroxy carboxylic acids, for example ω-hydroxy caproic acid, may also be used.

The polyethers containing at least two, generally from 2 to 8, preferably 2 or 3, hydroxyl groups which may be used in accordance with the present invention are also known and are obtained, for example, by the polymerization of epoxides, such as ethylene oxide, propylene oxide, butylene oxide, tetrahydrofuran, styrene oxide or epichlorohydrin, on their own, for example in the presence of $BF_3$, or by the chemical addition of these epoxides, optionally in admixture or in succession, to starter components containing reactive hydrogen atoms. Such starter compounds include water, alcohols or amines, such as ethylene glycol, 1,3- or 1,2-propylene glycol, trimethylol propane, 4,4'-dihydroxy diphenyl propane, aniline, ammonia, ethanolamine and ethylene diamine. In many cases, it is preferred to use polyethers of the type which contain major amounts of primary OH groups (up to 90%, by weight, based on all the OH groups present in the polyether). Polyethers modified by vinyl polymers of the type obtained, for example, by the polymerization of styrene, acrylonitrile in the presence of polyethers (U.S. Pat. Nos. 3,383,351; 3,304,273; 3,523,093 and 3,110,695, German Pat. No. 1,152,536) as well as polybutadienes containing OH-groups are also suitable.

Among the polythioethers, particular reference is made to the condensation products of thiodiglycol with itself and/or with other glycols, dicarboxylic acids, formaldehyde, amino carboxylic acids or amino alcohols. Depending upon the co-components, these products are polythio mixed ethers, polythioether esters, or polythioether ester amides.

Suitable polyacetals include those compounds which may be obtained from the reaction of glycols, such as diethylene glycol, triethylene glycol 4,4'-dioxethoxy diphenyl dimethyl methane and hexane diol, with formaldehyde. Polyacetals suitable for the purposes of the present invention may also be obtained by polymerizing cyclic acetals.

Suitable polycarbonates containing hydroxyl groups are those known compounds obtainable, for example, by reacting diols, such as 1,3-propane diol, 1,4-butane diol and/or 1,6-hexane diol, diethylene glycol, triethylene glycol and tetraethylene glycols, with diaryl carbonates, for example diphenyl carbonate, or with phosgene.

Examples of the polyester amides and polyamides are the predominantly linear condensates obtained from polybasic, saturated and unsaturated carboxylic acids and the anhydrides thereof and polyfunctional saturated and unsaturated amino alcohols, diamines, polyamines and mixtures thereof.

Polyhydroxyl compounds already containing urethane or urea groups and optionally modified natural polyols, such as castor oil, carbohydrates, starch, may also be used. Addition products of alkylene oxides with phenolformaldehyde resins or even with urea-formaldehyde resins may also be used.

Representatives of the many and varied compounds used in accordance with the present invention are generally known and are described, for example, in High Polymers, Vol. XVI, "Polyurethanes, Chemistry and Technology", by Saunders-Frisch, Interscience Publishers, New York, London, Vol. I, 1962, pages 32 to 42 and pages 44 to 54, and Vol. II, 1964, pages 5 to 6 and 198–199, and in Kunststoff-Handbuch, Vol. VII, Vieweg-Hochtlen, Carl Hanser-Verlag, Munich, 1966, pages 45 to 71.

It is, of course, also possible to use mixtures of the above-mentioned compounds containing at least two isocyanate-reactive hydrogen atoms and having a molecular weight of from 800 to 10,000, for example mixtures of polyethers and polyesters.

Other starting components which may optionally be used in the present invention are compounds containing at least two isocyanate-reactive hydrogen atoms and having molecular weights of from 32 to 400. In this case the compounds in question are also compounds containing hydroxyl groups and/or amino groups and/or thiol groups and/or carboxyl groups, preferably compounds containing hydroxyl groups and/or amino groups which are used as chain-extenders or cross-linkers. These compounds generally contain from 2 to 8 isocyanate-reactive hydrogen atoms, and preferably 2 or 3 such reactive hydrogen atoms.

Examples of such compounds are ethylene glycol, 1,2- and 1,3-propylene glycol, 1,4- and 2,3-butylene glycol, 1,5-pentane diol, 1,6- hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, trimethylol ethane, pentaerythritol, quinitol, mannitol, sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol, polybutylene glycols having a molecular weight of up to 400, 4,4'-dihydroxy diphenyl propane, dihydroxy methyl hydroquinone, ethanolamine, diethanolamine, triethanolamine, 3-aminopropanol, ethylene diamine, 1,3-diaminopropane, 1-mercapto-3-aminopropane, 4-hydroxy- and -amino-phthalic acid, succinic acid, adipic acid, hydrazine, N,N'-dimethyl hydrazine, 4,4'-diaminodiphenyl methane, tolylene diamine, methylene-bis-chloraniline, methylene-bis-anthranilic acid ester, diaminobenzoic acid esters and the isomeric chlorophenylene diamines.

It is also possible to use mixtures of different compounds containing at least two isocyanate-reactive hydrogen atoms and having a molecular weight of from 32 to 400.

It is also possible to use polyhydroxyl compounds containing high molecular weight polyadducts or polycondensates in finely dispersed or dissolved form. Such modified polyhydroxyl compounds are obtained by carrying out polyaddition reactions (for example reactions between polyisocyanates and aminofunctional compounds) or polycondensation reactions (for example between formaldehyde and phenols and/or amines) directly in situ in the abovementioned compounds containing hydroxyl groups. Such processes are known and are described, for example, in German Auslegeschriften No. 1,168,075 and 1,260,142 and in German Offenlegungsschriften Nos. 2,324,134; 2,423,984; 2,512,385; 2,513,815; 2,550,796; 2,550,797; 2,550,833 and 2,550,862. It is also possible, in accordance with U.S. Pat. No. 3,869,413 or German Offenlegungsschrift No. 2,550,860, to mix an aqueous polymer dispersion with a polyhydroxyl compound and subsequently to remove the water from the mixture. In cases where such modified polyhydroxyl compounds are used as starting component in the polyisocyanate polyaddition process, polyurethane plastics having considerably improved mechanical properties are formed in many cases.

The reaction of the polyhydroxyl compounds obtainable in accordance with the present invention (without the use of other isocyanate-reactive components) with strongly elasticizing polyisocyanates, such as polyisocyanates of biuret structure (German Auslegschrift No. 1,543,178), gives hard, light-stable, scratch resistant and solvent-resistant coatings and lacquers.

The present invention also relates to a process for the production of optionally cellular polyurethane plastics comprising reacting:
(a) polyisocyanates; with
(b) polyhydroxyl compounds having a molecular weight of less than 400; and, optionally,
(c) relatively high molecular weight polyhydroxyl compounds and/or other chain-extending agents, optionally in the presence of
(d) blowing agents, catalysts and other known additives;
wherein the formoses produced in accordance with the present invention or the formitols obtained from such formoses by reduction are used as component (b).

It is possible by propoxylating and/or oxyethylating the formoses or formitols of the present invention to obtain polyether alcohols of high functionality. In high OH-number ranges, these polyols can be used for the production of rigid or semi-rigid cellular polyurethane plastics. With low OH-numbers they are useful as starting materials for flexible polyurethane foams.

By reacting the mixtures of polyhydric alcohols produced in accordance with the present invention with polybasic carboxylic acids of the above-mentioned type, for example phthalic acid, isophthalic acid, terephthalic acid, tetra- and hexa-hydrophthalic acid, adipic acid or maleic acid, by the methods normally used for condensing polyesters, as described, for example in Houben-Weyl, Methoden der organischen Chemie, Vol. XIV 12, page 40, it is possible to synthesize strongly branched polyesters which improve the hardness of alkyd resins to which they are added. These polyesters containing hydroxyl groups which are synthesized from the hydroxyl compounds produced in accordance with the present invention are, of course, also suitable for use as starting components for the production of polyurethane plastics.

The polyhydric alcohols produced in accordance with the present invention and the hydroxy aldehydes and hydroxy ketones may also be reacted very easily with long-chain, aliphatic monocarboxylic acids to form esters containing hydroxyl groups. Such acids include caprylic acid, capric acid, lauric acid, myristic acid, palmitic acid, stearic acid, oleic acid, linoleic acid, arachidonic acid or behenic acid, or with derivatives thereof, such as the methyl or ethyl esters and also the anhydrides or mixed anhydrides. Like the ethoxylation products of the polyols or even reaction products of the polyhydroxyl compounds obtainable in accordance with the present invention with long-chain monoisocyanates, such as n-octyl, n-decyl, n-dodecyl, myristyl, cetyl or stearyl isocyanate, to form carbamic acid esters (cf. for example K. Lindner, Tenside, Vol. III, Wissenschaftliche Verlagsgesellschaft Stuttgart, 1964, page 2336), these esters containing hydroxyl groups are non-ionic surface-active compounds which may be used as valuable emulsifiers, wetting agents or plasticizers.

The compounds according to the present invention may also be used as humectants in cosmetics and plastics and, they may be used as antifreeze agents.

They may also be used as a carbohydrate-containing substrate in nutrient mediums of microorganisms. Process products consisting primarily of hydroxy aldehydes and hydroxy ketones containing 5 and 6 carbon atoms have proved to be particularly suitable for this purpose.

The process according to the present invention is illustrated by the following Examples, in which the figures quoted represent parts, by weight, and percent, by weight, unless otherwise indicated.

EXAMPLES

EXAMPLE 1

300 g of a fully desalted 25% aqueous formose solution produced in accordance with Example 1 of German Offenlegungsschrift No. 2,639,084 are introduced into a 2 liter capacity multi-necked flask provided with a distillation bridge plus receiver flask, a pH electrode, a stirrer and two dropping funnels. The aqueous formose is heated to from 95° to 97° C. 50 ml of a 37% formalin solution is then added to the boiling solution from one of the dropping funnels. After the boiling temperature of the mixture has been reached again, the heat source is removed. A 25% aqueous $Ca(OH)_2$ suspension is then added from the second dropping funnel in such a quantity that the pH of the mixture is adjusted to 9.8. As the $Ca(OH)_2$ added passes into solution, the reaction mixture becomes green to yellowish in color and begins to boil moderately in the absence of an additional heat source. After the reaction has started, $Ca(OH)_2$ suspension and formalin solution are simultaneously added at such a rate that the mixture is kept moderately boiling. The pH of the reaction solution remains in the range of from 8 to 9 and the formaldehyde concentration amounts to from 4 to 5%.

After 1000 g of the 37% formalin solution have been added, the addition of $Ca(OH)_2$ is stopped. The formaldehyde content of the mixture is determined to be 4.4%. After a total reaction time of 37 minutes, the formaldehyde content of the mixture has fallen to 3.3%. A total of 30 g of $Ca(OH)_2$ was added including all steps of the reaction.

The Ca is precipitated from the mixture by the addition of 199 g of 20% sulphuric acid. Filtration and concentration in vacuo leave 419 g (89% of the theoretical yield) of a light-colored formose which contains 5.5% of water and which has a sugar content, expressed as glucose, of 57.1%.

After hydrogenation of the formose and silylation of the resulting formitol, the following component distribution is determined by gas-chromatographic analysis:

| | $C_2$ | $C_3$ | $C_4$ | $C_5$ | $C_6$ | $C_7$ | $C_8$ |
|---|---|---|---|---|---|---|---|
| % | 0.10 | 1.04 | 5.60 | 13.38 | 39.42 | 33.49 | 6.98 |

COMPARISON EXAMPLE 1

500 g of 37% formalin solution and 150 g of a 30% fully desalted formose according to Example 1 of German Offenlegungsschrift No. 2,639,084 are mixed and heated to 60° C. The mixture has a pH value of 3.1. By adding 15 g of powdered $Ca(OH)_2$, the pH of the mixture is increased to 9.8. Under the effect of the spontaneously beginning, highly exothermic reaction, the reaction mixture undergoes a spontaneous increase in temperature to 80° C. It is then intensively cooled with a prepared ice bath. Despite intensive cooling, the reaction becomes increasingly more violent so that the reaction mixture spurted out of the reaction vessel through the reflux condenser and from a ground opening after a stopper had been blown out.

COMPARISON EXAMPLE 2

1000 g of a 37% formalin solution are mixed with 300 g of a fully desalted formose according to Example 1 of German Offenlegungsschrift No. 2,639,084 and the resulting mixture heated to 60° C. By adding 10 g of $Ca(OH)_2$, the pH value of the mixture is adjusted to from 7.5 to 8. More $Ca(OH)_2$ is then added at such a rate that the pH value of the mixture remains in this range. After a total of 96.5 hours, by which time 105 g of $Ca(OH)_2$ have been added, the formaldehyde content of the mixture has fallen to 0.

The reaction mixture is cooled and desalted over ion exchangers. Concentration in a rotary evaporator gives 317 g of a formose having a water content of 7.2% and a sugar content, expressed as glucose, of 10.5%.

After hydrogenation and silylation, the following component distribution is determined by gas chromatographic analysis:

| | $C_2$ | $C_3$ | $C_4$ | $C_5$ | $C_6$ | $C_7$ | $C_8$ |
|---|---|---|---|---|---|---|---|
| % | 0.084 | 0.762 | 10.15 | 5.17 | 27.49 | 49.46 | 6.87 |

This comparison Example shows the much longer reaction time and lower sugar yield obtained when the pH profile deviates from the process according to the present invention.

EXAMPLE 2

75 g of pure glucose and 225 g of water are introduced into a 2 liter capacity multi-necked flask equipped with a distillation bridge plus receiver flask, a pH electrode, a stirrer and two dropping funnels. The aqueous solution is heated to 95° C. 50 ml of a 37% formalin solution are then added to the boiling solution from one of the dropping funnels. After the boiling temperature of the mixture has been reached again, the heat source is removed. A 25% aqueous $Ca(OH)_2$ suspension is then added from the second dropping funnel in such a quantity that the pH value of the mixture is adjusted to 9.2. The $Ca(OH)_2$ added passes into solution, the reaction mixture becomes yellowish in color and begins to boil moderately in the absence of an additional heat source. After the reaction has started, $Ca(OH)_2$ suspension and formalin are simultaneously added at such a rate that the mixture is kept moderately boiling.

The pH value of the solution is kept at from 8 to 9 and the formaldehyde concentration amounts to from 3 to 4%.

After 1000 g of formalin solution have been added, the addition of Ca(OH)$_2$ is stopped. After a total reaction time of 30 minutes, the formaldehyde content of the mixture has fallen to 2%. A total of 22.5 g of Ca(OH)$_2$ has been added.

The Ca is precipitated from the mixture by the addition of 149 g of 20% sulphuric acid. A light-colored formose is obtained after filtration and concentration in vacuo.

A total of 24 g of aqueous methanol containing 2.2% of formaldehyde distills off during the reaction.

What is claimed is:

1. In a process for the production of low molecular weight polyhydroxyl compounds by condensing formaldehyde hydrate in the presence of calcium hydroxide as catalyst and in the presence of compounds capable of enediol formation as co-catalyst, the improvement which comprises adjusting a formaldehyde-containing solution of the co-catalyst in water to a pH value of from 9 to 12 by the addition of calcium hydroxide at a temperature of from 80° to 110° C. so that concensation of the formaldehyde hydrate is started, and then adding to this reaction mixture, (1) an aqueous formalin solution and/or paraformaldehyde dispersion containing from 20 to 65%, by weight, of formaldehyde, and (2) calcium hydroxide at such a rate that the reaction mixture is maintained at a pH value of from 7.5 to 9.5 at a temperature of from 80° to 110° C., the concentration of formaldehyde being maintained at from 0.5 to 10%, by weight, based on the total reaction mixture, throughout the condensation reaction.

2. The process of claim 1 wherein low molecular weight monohydric or polyhydric alcohols and/or relatively high molecular weight polyhydroxyl compounds are present in the reaction mixture containing the formaldehyde-containing solution of the co-catalyst in water when the condensation of the formaldehyde hydrate is started.

3. The process of claim 1 wherein the formaldehyde residue, amounting to from 0.5 to 10% by weight is removed by further condensation at pH values below 7 or by reaction with other compounds that are reactive with formaldehyde hydrate.

4. The process of claim 1 wherein a pH value of from 9 to 10 is maintained during the starting phase of the reaction and is subsequently adjusted to from pH 8 to 9.

5. The process of claim 1 wherein the concentration of formaldehyde is maintained at from 1.2 to 6%, by weight, throughout the condensation reaction.

6. The process of claim 1 wherein formose is used as the co-catalyst during the starting phase of the condensation reaction.

7. The process of claim 6 wherein said formose has the following molar ratios:
Compounds containing 3 carbon atoms/compounds containing 4 carbon atoms: 0.5:1–2.0:1
Compounds containing 4 carbon atoms/compounds containing 5 carbon atoms: 0.2:1–2.0:1
Compounds containing 5 carbon atoms/compounds containing 6 carbon atoms: 0.9:1–5.0:1
the proportion of components containing from 3 to 6 carbon atoms amounting to at least 75% by weight.

8. The process of claim 1 wherein the calcium hydroxide is added at a temperature of from 90° to 105° C.

9. The process of claim 1 including the additional subsequent step of reacting the reaction product with excess formaldehyde for about 10 minutes to 12 hours at a pH of from 9 to 13 at temperatures of from 10° to 100° C.

10. The process of claim 9 wherein reaction product is reacted with excess formaldehyde at a pH of from 10 to 11 and a temperature of from 30° to 60° C.

11. The process of claim 1 wherein the reaction product is reduced by reaction with sodium borohydride, electrolytically, or by catalytic hydrogenation.

* * * * *